United States Patent
Park et al.

(10) Patent No.: US 6,713,290 B2
(45) Date of Patent: Mar. 30, 2004

(54) PROCESS FOR PREPARING OPTICALLY PURE (S)-3-HYDROXY-γ-BUTYROLACTONE

(75) Inventors: Young Mi Park, Daejeon (KR); Jongpil Chun, Daejeon (KR); Yik-haeng Cho, Daejeon (KR); Kyoung Rok Roh, Daejeon (KR); Hosung Yu, Daejeon (KR); Dae Hwang, II, Daejeon (KR)

(73) Assignee: Samsung Fine Chemicals Co., Ltd. (KR)

( * ) Notice: Subject to any disclaimer, the term of this patent is extended or adjusted under 35 U.S.C. 154(b) by 0 days.

(21) Appl. No.: 09/946,449

(22) Filed: Sep. 6, 2001

(65) Prior Publication Data

US 2002/0048796 A1 Apr. 25, 2002

Related U.S. Application Data

(63) Continuation of application No. 09/359,677, filed on Jul. 23, 1999, now abandoned.

(30) Foreign Application Priority Data

Jul. 24, 2001 (KR) .............................. 98-29912

(51) Int. Cl.[7] ........................ C12P 17/04; C07D 307/33
(52) U.S. Cl. ........................ 435/126; 435/72; 435/74; 435/99; 549/313
(58) Field of Search .................. 435/126, 72, 74, 435/99; 549/313

(56) References Cited

U.S. PATENT DOCUMENTS

| | | |
|---|---|---|
| 3,791,865 A | 2/1974 | Hurst et al. |
| 3,922,200 A | 11/1975 | Guillaume et al. |
| 3,986,890 A | 10/1976 | Richter et al. |
| 4,138,484 A | 2/1979 | Fuxe |
| 4,199,372 A * | 4/1980 | Walon .................. 127/40 |
| 4,447,532 A | 5/1984 | Coker et al. |
| 4,612,284 A | 9/1986 | Pickens et al. |
| 4,855,232 A | 8/1989 | Takasaki |
| 4,971,906 A | 11/1990 | Melasuiemi et al. |
| 5,266,467 A | 11/1993 | Inglett |
| 5,292,939 A * | 3/1994 | Hollingsworth ............. 562/515 |
| 5,319,110 A | 6/1994 | Hollingsworth |
| 5,374,773 A | 12/1994 | Hollingsworth |
| 5,506,353 A | 4/1996 | Subramaniam |
| 5,527,699 A * | 6/1996 | Nakano et al. ............. 435/201 |
| 5,808,107 A | 9/1998 | Hollingsworth |
| 6,124,122 A * | 9/2000 | Chun et al. .................. 435/126 |
| 6,251,642 B1 * | 6/2001 | Chun et al. .................. 435/126 |

FOREIGN PATENT DOCUMENTS

| | | |
|---|---|---|
| EP | 451142 A2 | 10/1991 |
| JP | 64-13069 | 1/1989 |
| JP | 4-149151 | 5/1992 |
| JP | 4-158795 | 6/1992 |
| JP | 6-172256 | 6/1994 |
| WO | WO 93/06826 | 4/1993 |
| WO | WO 94/05639 | 3/1994 |
| WO | WO 98/04543 | 5/1998 |
| WO | WO 99/05092 | 4/1999 |

OTHER PUBLICATIONS

Saito, Archives of Biochemistry and Biophysics, 155:290–298 (1973).
The Condensed Chemical Dictionary, Hawley, editor, Van Nostrand Reinhold Company, New York, p. 644 (1971).
J. Am. Chem. Soc., 105, 5925–5926 (1983).
J. Am. Chem. Soc., 117, 1181 (1995).
J. Am. Chem. Soc., 2245–2247 (1953).
J. Chem. Soc., 1924–1931 (1960).
J. Chem. Soc., 1932–1938 (1960).
J. Am. Chem. Soc., 1431–1435 (1955).
J. Am. Chem. Soc., 81, 3136 (1959).
Bull. Chem. Soc. Jpn., 61, 2025 (1988).
J. Org. Chem., 50, 1144 (1985).
Tetrahedron Letter, 46, 4277 (1990).
Tetrahedron Letter, 33, 2279 (1992).
Tetrahedron Letter, 507 (1992).
Tetrahedrom Letter, 31, 267–270 (1990).
Chem. Lett., 1389–1392 (1984).
J. Res. Natl. Bur. Standards., vol. 32, No.2, p. 45 (1944).
Can. J. Chem., 65, 195 (1987).
Carbohyd. Res., 11, 17–25 (1969).
Starch 41 Nr. 8, S. 303–309 (1989).
Synthesis, 597–613 (1997).
J. Chromatography, 549, 113–125 (1991).
Encyclopedia of Chemical Technology 3$^{rd}$ ed. 491–507.
Methods Carbohydr. Chem., 10, 231–239 (1994).
Methods Carbohydr. Chem. 10, 245–248 (1994).

* cited by examiner

Primary Examiner—Francisco Prats
(74) Attorney, Agent, or Firm—Finnegan, Henderson, Farabow, Garrett & Dunner, L.L.P.

(57) ABSTRACT

The present invention relates to a process for preparing optically pure (S)-3-hydroxy-γ-butyrolactone expressed by the following Formula 1 and more particularly, to a process that enables preparing optically pure (S)-3-hydroxy-γ-butyrolactone economically in large quantities, by:

(a) Preparing α-(1,4) linked oligosaccharide with adequate sugar distribution by reacting starch which is easily available from natural product with enzyme under a specific condition; and (b) Performing oxidation and cyclization sequentially under a specific condition.

(1)

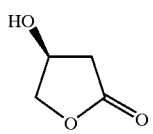

24 Claims, 3 Drawing Sheets

PROCESS FOR PREPARING OPTICALLY PURE (S)-3-HYDROXY-γ-BUTYROLACTONE

CROSS-REFERENCE TO RELATED APPLICATIONS

This is a continuation division of application Ser. No. 09/359,677, filed Jul. 23, 1999, now abandoned which is incorporated herein by reference.

BACKGROUND OF THE INVENTION

1. Field of the Invention

The present invention relates to a process for preparing optically pure (S)-3-hydroxy-γ-butyrolactone expressed by the following Formula 1 and more particularly, to a process that enables preparing optically pure (S)-3-hydroxy-γ-butyrolactone economically in large quantities by:

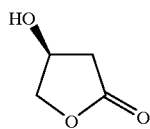

(1)

preparing α-(1,4) linked oligosaccharide having adequate sugar distribution by reacting starch which is easily available from natural product with enzyme under a specific condition; and performing oxidation and cyclization sequentially under a specific condition.

2. Description of the Related Arts (S)-3,4-Dihydroxybutyric acid derivatives and (S)-3-hydroxy-γ-butyrolactone are used as synthetic intermediates for preparing various chiral compounds. For example, it is well known that they act as key intermediates for preparing neuromeidator (R)-GABOB [*Tetrahedron*, 46, 4277(1990)], treatment for hyperlipemia (Atorvastatin; HMG-CoA reductase inhibitor) [*Tetrahedron Lett.*, 33, 2279(1992)], (S)-oxiracetam which is improvement agent in brain metabolism [International patent publication WO93/06,826], L-carnitine which is health supplement agent [International patent publication WO99/05,092], (S)-3-hydroxytetrahydrofuran [*J. Am. Chem. Soc.*, 117, 1181(1995); International patent publication WO94/05,639] which is an essential intermediate of AIDS drug (Agenerase; HIV protease inhibitor), (S)-monobetalactam [Japanese patent publication 64-13,069(1989)], ester of (S)-3-hydroxy-4-bromobutyric acid [Japanese patent publication 4-149,151(1992); Japanese patent publication 6-172,256(1994)], potentiating intermediate of satiety agent [*Bull. Chem. Soc. Jpn.*, 61, 2025(1988)] and neuroleptic drug [U.S. Pat. No. 4,138,484] and useful intermediates in synthetic efforts towards natural products [*J. Org. Chem.*, 50, 1144 (1985); *Can. J. Chem.*, 65, 195 (1987), *Tetrahedron Lett.*, 507 (1992)]. Optical purity is the most important factor in preparing these chiral compounds.

The conventional technologies for preparing (S)-3,4-dihydroxybutyric acid derivatives and (S)-3-hydroxy-γ-butyrolactone, which are useful for preparing the said chiral compounds, are explained in detail hereunder.

Methods of preparing (S)-3-hydroxybutyric acid derivatives from the enzymatic or catalytic reduction of β-ketoester were known [*J. Am. Chem. Soc.*, 105, 5925–5926(1983); *Teterahedron Lett.*, 31, 267–270(1990); European patent publication 452,143A2]. These methods have difficulty in that the prochiral center should be reduced to one-side to generate chiral center and expensive metal catalyst should be used.

A technology preparing ester of (S)-3,4-dihydroxybutyric acid and (S)-3-hydroxy-γ-butyrolactone by selective reduction of (L)-malic acid ester was known [*Chem. Lett.*, 1389–1392(1984); U.S. Pat. No. 5,808,107]. This technology has disadvantage in that reduction should be performed selectively to only one of the two ester functional groups.

Many methods of preparing (S)-3,4-dihydroxybutyric acid derivatives and (S)-3-hydroxy-γ-butyrolactone from carbohydrate have been reported.

A technology preparing isosaccharinic acid (B) or (S)-3,4-dihydroxybutyric acid (C) is reported [*J. Chem. Soc.*, 1924–1931(1960)] by alkaline degradation of carbohydrate containing glucose substituent in the 4-position, such as 4-O-methyl-(D)-glucose, maltose, amylose and cellulose, elimination of C-4 substituent as leaving group, forming dicarbonyl compound (A; 4-deoxy-2,3-hexodiulose), and reacting the formed dicarbonyl compound with base as shown in Scheme 1. However, the yield of (S)-3,4-dihydroxybutyric acid is low.

Scheme 1

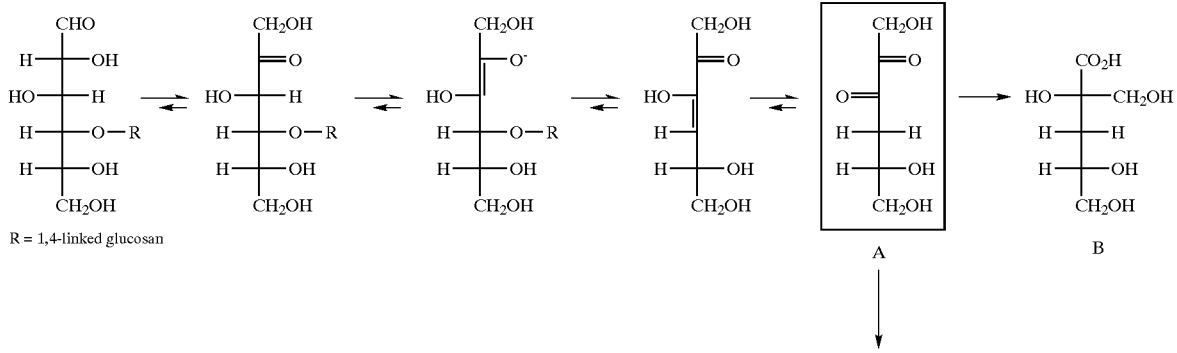

R = 1,4-linked glucosan

-continued

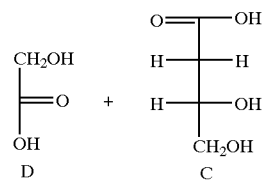

Also, it has been reported that (S)-3,4-dihydroxybutyric acid (C) and glycolic acid (D) were obtained as major products by forming dicarbonyl compound (A) from alkaline degradation of carbohydrate containing glucose substituent in the 4-position, and separating the formed dicarbonyl compound (A) and reacting it with hydrogen peroxide [*J. Chem. Soc.*, 1932–1938(1960)]. This method has a serious problem that the product exists as small amount of isomers due to tautomerization and a mixture of cyclic compounds and hydrates derived from dicarbonyl compound (A). So, the dicarbonyl compound (A) cannot be separated in good yields from the reaction mixture. Another problem is that the prepared (S)-3,4-dihydroxybutyric acid is degraded to formic acid and glycolic acid due to the overoxidation.

A similar technology for preparing (S)-3,4-dihydroxybutyric acid from carbohydrate either using base only or using oxygen in base was known. It proposed that the dicarbonyl compound (A) was a synthetic intermediate for (S)-3,4-dihydroxybutyric acid as shown in the Scheme 1. But the yield was reported to be as low as about 30% [*J. Res. Natl. Bur. Stand.*, 32, 45(1944); *J. Am. Chem. Soc.*, 2245–2247(1953); *J. Am. Chem. Soc.*, 1431–1435(1955); *Carbohyd. Res.*, 11, 17–25(1969); *J. Chromatography*, 549, 113–125(1991)]. In these methods, (S)-3,4-dihydroxybutyric acid is produced with various kinds of mixtures including glycolic acid (D), isosaccharinic acid (B), formic acid, ketone, diketone and glyceric acid. Since the yield of (S)-3,4-dihydroxybutyric acid is very low, these methods are also considered as not suitable for industrial use.

A method for preparing (S)-3,4-dihydroxybutyric acid from disaccharide (lactose) using base and oxidant has been reported [International patent publication WO98/04543]. In this work, (S)-3,4-dihydroxybutyric acid was cyclized to (S)-3-hydroxy-γ-butyrolactone under the reaction condition and purified by protection of the two hydroxy groups to acetonide ester compound, methyl (S)-3,4-O-isopropylidene-3,4-dihydroxybutanoate, which was recyclized to (S)-3-hydroxy-γ-butyrolactone under acidic media.

Preparing methods of (S)-3,4-dihydroxybutyric acid including the process of alkaline oxidation of carbohydrate containing glucose substituent in the 4-position have been known [U.S. Pat. Nos. 5,292,939, 5,319,110 & 5,374,773 (1994)]. In these methods, dicarbonyl compound (A) intermediate is formed at first, oxidized to (S)-3,4-dihydroxybutyric acid (C) and glycolic acid (D). However, optical purity, the most important physical property of chiral compounds, is not mentioned at all. Also, purification of target compound is very difficult, considering the reaction mechanism. In the case of disaccharides such as maltose or lactose, only one sugar unit in the disaccharide forms (S)-3,4-dihydroxybutyric acid and the other sugar unit functions as leaving group, so that the target product and leaving group coexist as 1:1 mixture. Accordingly, it is very difficult to separate and purify (S)-3,4-dihydroxybutyric acid or (S)-3-hydroxy-γ-butyrolactone from the reaction mixture.

The maximum mass conversion obtainable is 28.3 wt. %. In other words, 28.3g of (S)-3-hydroxy-γ-butyrolactone can be obtained from 100 g of disaccharide. For polysaccharides, such as maltodextrin, starch and cellulose, mentioned in the above patents, the (1,4) and/or (1,6) glucose units are linked complexly like nets. The problem is that the step-by-step oxidation proceeding from the reducing end units comprising (1,4) linkage terminates at (1,6) linkage unit. Therefore, no more target product is formed. Also, the polysaccharides are degraded by overoxidation of reducing end units to complex acid mixtures containing formic acid, oxalic acid, glycolic acid and erythronic acid [*J. Am. Chem. Soc.*, 81, 3136(1959); *Starch*41 Nr. 8, S. 303–309(1989); *Synthesis*, 597–613(1997)].

There was an attempt to improve the yield of (S)-3,4-dihydroxybutyric acid or (S)-3-hydroxy-γ-butyrolactone for polysaccharide by degradation of higher-molecular sugars to relatively lower-molecular sugars through acid or base hydrolysis. Though the reactivity by this method is increased to a degree, (1,4) linkage and (1,6) linkage are not hydrolyzed selectively to afford random distribution. Accordingly, there is a fundamental problem in preparing (S)-3,4-dihydroxybutyric acid derivatives in high yield [*Encyclopedia of Chemical Technology*, 3rd ed. 492–507].

Regarding the preparation of (S)-3-hydroxy-γ-butyrolactone using (1,4) linked polysaccharide, the step-by-step oxidation proceeds continuously from the reducing end units to non-reducing end units to afford (S)-3,4-dihydroxybutyric acid until the last chain unit (leaving group) remains. Namely, if (1,4)-linked polysaccharide is used as a source material for preparing (S)-3-hydroxy-γ-butyrolactone, the maximum mass conversion obtainable is 63 wt. %, about two times more compared with the method using disaccharide. In other words, 63 g of (S)-3-hydroxy-γ-butyrolactone can be obtained from 100 g of (1,4)-linked polysaccharide. Also, since the small amount of leaving group is produced in the reaction mixture compared with disaccharide, the target product is easily purified. Therefore, the use of (1,4)-linked polysaccharide promises the enhanced productivity.

However, regarding conventional polysaccharides, the target product and by-products (acids such as formic acid, oxalic acid, glycolic acid and erythronic acid) are formed competitively in the step-by-step oxidation due to the compact structure having random (1,4) linkage and (1,6) linkage. Thus, selective degradation technique of polysaccharide to a suitable sugar distribution range having (1,4) linkage is required.

On the other hand, there have been many reports of transforming higher-molecular sugars to lower-molecular sugars using biological enzymatic treatment process for industrial use.

The reported technologies include preparing glucose, maltose and ethanol through enzymatic treatment of starch [U.S. Pat. No. 3,791,865(1974); U.S. Pat. No. 3,922,200 (1975); U.S. Pat. No. 4,855,232(1989): Japanese patent publication 4-158,795(1992); *Methods Carbohydr. Chem.*, 10, 231–239(1994); *Methods Carbohydr. Chem.*, 10, 245–248(1994)], and preparing maltodextrin with adequate dextrose equivalent (DE) [U.S. Pat. No. 3,986,890(1976); U.S. Pat. No. 4,447,532(1984); U.S. Pat. No. 4,612,284 (1986); U.S. Pat. No. 5,506,353(1996)]. In these references, through the degradation or transformation of high molecular polysaccharides, they are converted to adequate materials for medicines, food additives and diagnostic reagents.

But, the method for preparing (1,4)-linked oligosaccharides suitable for the mass production of (S)-3-hydroxy-γ-butyrolactone by biological treatment of higher molecular polysaccharides with enzymes is not known at present.

SUMMARY OF THE INVENTION

The inventors of the present invention made intensive efforts to develop a method for preparing optically pure (S)-3-hydroxy-γ-butyrolactone from commercially available starch with ease. As a results, a process which enables preparing optically pure (S)-3-hydroxy-γ-butyrolactone economically in large quantities is found by preparing oligosaccaride with structural specificity which can minimize formation of by-products from starch by enzymatic reaction. Furthermore, oxidation reaction can be performed continuously in the same reactor without additional separation and purification of the prepared oligosaccharide.

Accordingly, an object of this invention is to provide a method for preparing optically pure (S)-3-hydroxy-γ-butyrolactone in high yield without additional purification of intermediates.

DETAILED DESCRIPTION OF THE INVENTION

Figure 1A:
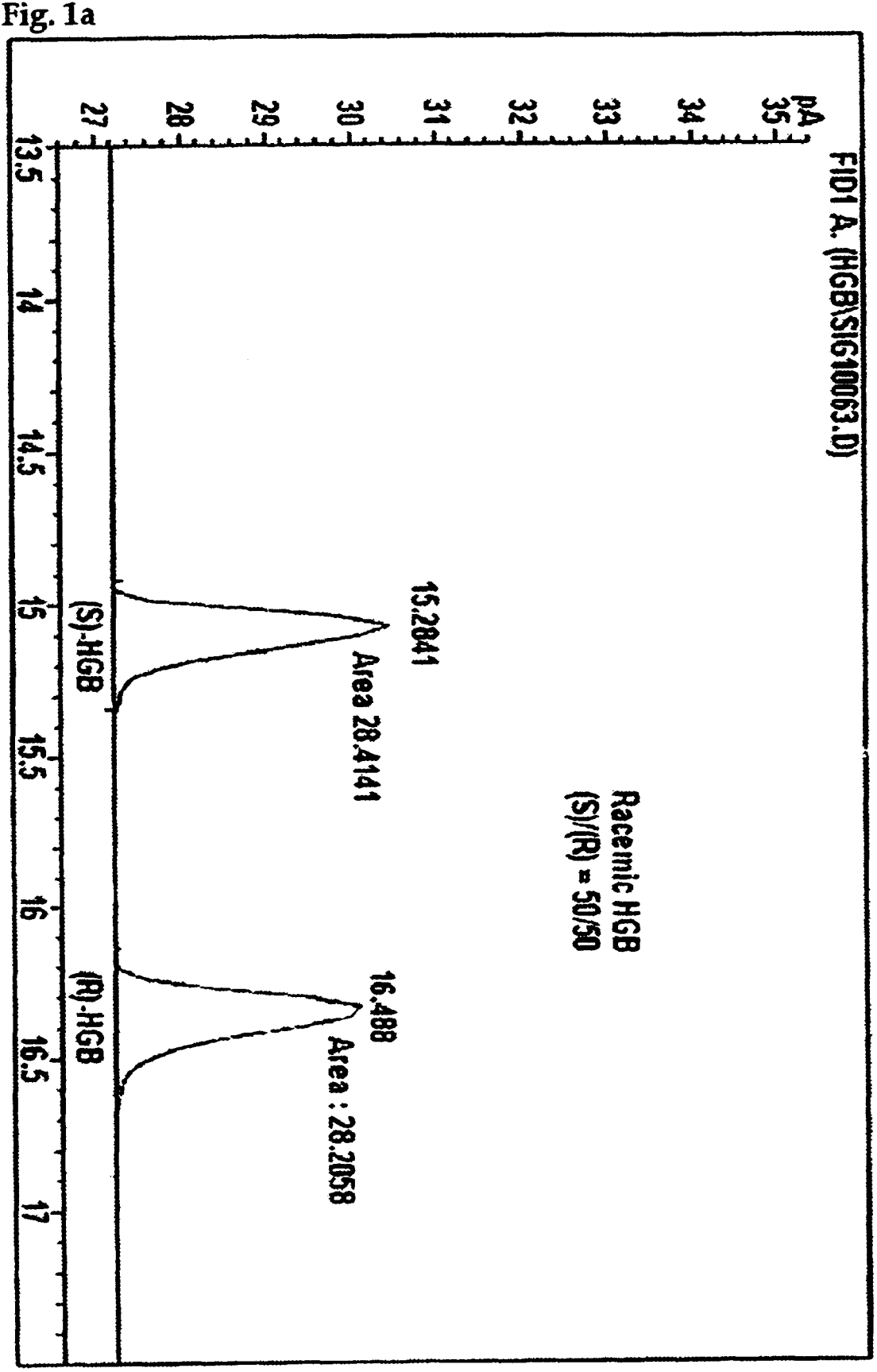
FIG. 1a represents the optical purity analysis results by gas chromatography (GC) of racemic 3-hydroxy-γ-butyrolactone.

The present invention is characterized by comprising the following steps:

enzymatic reaction of starch to α-(1,4)-linked oligosaccharide expressed by the Formula 2;

oxidation of the oligosaccharide with oxidant in base to afford the corresponding salt of (S)-3,4-dihydroxybutyric acid expressed by the Formula 3; and cyclization of the prepared salt of (S)-3,4-dihydroxybutyric acid in the presence of an acid catalyst without additional separation and purification process to afford (S)-3-hydroxy-γ-butyrolactone expressed by the Formula 1.

(1)

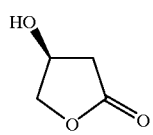

-continued

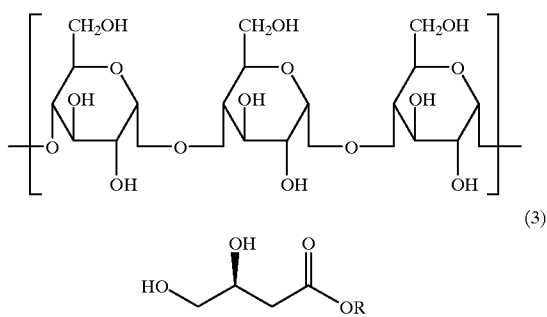

wherein, R represents an alkali metal atom or an alkaline earth metal atom.

The detailed description of the present invention is given hereunder.

The fundamental inventive concept of the present invention is selective degradation of α-(1,4) linkage and α-(1,6) linkage within starch using specific enzymes, i.e., transforming starch to α-(1,4) linked oligosaccharide with the optimal sugar distribution for preparing the target compound. And subsequently oxidation and cyclization are performed to prepare (S)-3-hydroxy-γ-butyrolactone.

Namely, focusing on the specificity of enzymes, starch is degraded sequentially with specific enzymes to α-(1,4) linked oligosaccharide, and optically pure (S)-3-hydroxy-γ-butyrolactone is prepared from the transformed oligosaccharide in high yield.

Starch, source material of the present invention, is commercially easily available. Especially, since starch is highly soluble in water or in buffer solution of pH 4.0–8.0, used as reaction solvent for enzymatic reaction of the present invention, the relative reactivity to enzyme is greatly increased compared with other polysaccharides such as cellulose. Thus, the same is very effective material for preparing of oligosaccharide having suitable sugar distribution for the preparation of (S)-3-hydroxy-γ-butyrolactone.

When using pullulanase as an enzyme for selective degradation of α-(1,6) linkage in starch, it causes the solubility problem of starch and reduced enzyme activity. So, rather than using pullulanase only, α-amylase was used to improve reactivity in degrading starch to a suitable sugar distribution, and then pullulanase was used. However, in this case, activity of the remaining α-amylase persists and thus α-(1–4) linkage in starch is degraded excessively, so that the desired oligosaccharide is not formed. Accordingly, a technology of inactivating the remaining α-amylase before the pullulanase reaction was introduced.

The detailed explanation of the preparation process of this invention is as follow. It comprises; 1) a step preparing oligosaccharide with characteristic α-(1,4) linkage expressed in Formula 2 by selective degradation of starch using biological treatment of specific enzymes, 2) a step preparing a metal salt of (S)-3,4-dihydroxybutyric acid through oxidation, and 3) a step preparing optically pure (S)-3-hydroxy-γ-butyrolactone in high yield through cyclization of the prepared salt compound under acid condition. Especially, the preparation process of this invention is characterized by preparing (S)-3-hydroxy-γ-butyrolactone in the same reactor without additional purification of the intermediates (oligosaccharide and salt of (S)-3,4-dihydroxybutyric acid).

The enzymatic reaction of the present invention uses α-amylase and pullulanase sequentially. α-Amylase degrades α-(1,4) linkage and pullulanase degrades α-(1,6) linkage selectively.

The superiority of the present invention lies in that optically pure (S)-3-hydroxy-γ-butyrolactone is prepared in high yield under a mild reaction condition by using enzymes selectively degrading α-(1,4) linkage or α-(1,6) linkage, while the chemical hydrolysis method has no selectivity.

The enzymatic reaction of the present invention is performed in water or buffer solution of pH 4.0–8.0 at 40–120° C. α-Amylase is used in the range of 0.001–10 wt. % of starch, and enzymatic reaction of α-amylase is performed for 30 min–4 hr, and then remaining α-amylase is inactivated. Inactivation is performed under acidic (pH 2.0–4.5) and high temperature (60–150° C.) conditions and maintained for 10 min–4 hr. In the enzymatic reaction of pullulanase, pullulanase is used in the range of 0.001–10 wt. % of starch, and most of the oligosaccharides distribute within 3–50 glucose units by 10–40 hr of the pullulanase enzymatic treatment. Reducing end units and molecular weight distribution of the prepared oligosaccharide are analyzed from reducing end units and dextrose equivalent analysis by an optical analyzer, HPLC analysis, and gel permeation chromatography (GPC) analysis.

The oligosaccharide is obtained from the selective enzymatic reaction and has distribution mostly between 3–50 glucose units, and preferably 5–50 glucose units. Since most of the glucose units are linked with α-(1,4) linkage, (S)-3-hydroxy-γ-butyrolactone can be obtained in high yield through continuous sequential reactions with minimizing the by-products (e.g., acid mixtures of formic acid, oxalic acid, glycolic acid and erythronic acid). Furthermore, the obtained (S)-3-hydroxy-γ-butyrolactone was identified to be optically very pure (>99.9%ee).

Oxidation of oligosaccharide is performed by adding base and oxidant dropwise for 6–36 hr under the condition of 30–65° C. Hydrogen peroxide, alkali metal peroxides, alkaline earth metal peroxides and alkyl hydroperoxides are used for the oxidants, and hydrogen peroxide is the most preferable. The oxidant is used in the range of 1–3 equivalents per molar glucose unit of starch. The base is selected from the group consisting of alkali metal hydroxide or alkaline earth metal hydroxide, and sodium hydroxide or potassium hydroxide is preferable. The base is used in the range of 1–3 equivalents per molar glucose unit of starch.

The preparation yields of (S)-3-hydroxy-γ-butyrolactone depending on the source material are compared as follows [Refer to Experimental example 1.]. If maltose (disaccharide) or lactose (disaccharide) obtained from cheese byproduct is used as source material, the theoretical mass conversion yield of (S)-3-hydroxy-γ-butyrolactone is not more than 28.3 wt. % of the source material weight used. On the other hand, if amylose (α-(1,4) linked polysaccharide) with more than 50 glucose units is used, the theoretical mass conversion yield of (S)-3-hydroxy-γ-butyrolactone is equal to that of starch. But, the double helix structure due to very strong intramolecular hydrogen bond limits the step-by-step oxidation, so the yield becomes very low. However, by using oligosaccharide of the present invention as source material, the yield of (S)-3-hydroxy-γ-butyrolactone is very high as 57.2 wt. % of the source material weight used.

(S)-3-hydroxy-γ-butyrolactone is prepared from the prepared salt of (S)-3,4-dihydroxybutyric acid by cyclization at the temperature range of 30–80° C. under reduced pressure in acidic conditions (pH=1–3). At least one inorganic acid, such as hydrochloric acid, sulfuric acid, phosphoric acid and nitric acid, or organic acid, such as fluoroalkylsulfonic acid, aralkylsulfonic acid, hydrate of aralkylsulfonic acid and trifluoroacetic acid, is used for the acid catalyst.

As explained above, the present invention is excellent in that the low reactivity of starch to oxidation is overcome by transforming starch to oligosaccharide with the application of specific enzymes. Furthermore, byproduct formation is minimized and optically pure (S)-3-hydroxy-γ-butyrolactone can be prepared in high yield with very simple purification process.

The following examples are intended to be illustrative of the present invention and should not be construed as limiting the scope of this invention defined by the appended claims.

EXAMPLE 1

Preparation of Sodium Salt of (S)-3,4-dihydroxybutyric Acid

10 L of water and 5 kg of dried starch were put into a 50 L reactor. After heating the reactor to 55° C., 12 g of α-amylase (BAN; EC 3.2.1.1 from *Bacillus licheniformis*, Novo Nordisk) was added. After heating this reaction solution to 75° C., the same was stirred for 2 hr at the same temperature. 5 mL of 0.1N HCl solution was added to adjust the pH of the reaction solution to 3.0–3.5, and then the same was stirred for 1 hr at 90° C. to inactivate the remaining α-amylase. After slowly cooling the reaction mixture to 30° C., 3.7 L of 4M acetic acid buffer solution (pH 5) and 1.3 L of water were added to adjust the pH to 5. The reaction solution was heated to 60° C., and then 62.5 g of pullulanase (Promozyme; EC 3.2.1.4 from *Bacillus acidopullulyticus*, Novo Nordisk) was added and the solution was stirred for 22 hr at the same temperature. 0.54 kg of 40% NaOH solution was added to the reaction solution to neutralize acetic acid and the temperature was raised to 60° C. 40% NaOH (8.64 kg) solution and 30% $H_2O_2$ (5.25 kg) solution were added dropwise for 24 hr to the reaction solution and the same was stirred for 1 hr at the same temperature. The formation of sodium salt of (S)-3,4-dihydroxybutyric acid (conversion ratio: 92%) was identified through NMR analysis with the comparison of internal standard.

$^1$H-NMR ($D_2O$, ppm) δ 2.27 (dd, 1H), 2.39 (dd, 1H), 3.41 (dd, 1H), 3.51 (dd, 1H), 3.8–3.9 (m, 1H)

EXAMPLE 2

Preparation of (S)-3-hydroxy-γ-butyrolactone

10 L of water and 5 kg of dried starch were put into a 50 L reactor. After heating the reactor to 55° C., 12 g of α-amylase (Teramyl; EC 3.2.1.1 from *Bacillus amyloliquefaciens*, Novo Nordisk) was added. After heating this reaction solution to 85° C., the same was stirred for 2 hr at the same temperature. 5 mL of 0.1N HCl solution was added to adjust the pH of the reaction solution to 3.0–3.5, and then the same was stirred for 1 hr at 90° C. to inactivate the remaining α-amylase. After slowly cooling the reaction to 30° C., 3.7 L of 4M acetic acid buffer solution (pH 5) and 1.3 L of water were added to adjust the pH to 5. The reaction solution was heated to 60° C., and then 62.5 g of pullulanase (Promozyme; EC 3.2.1.4 from *Bacillus acidopullulyticus*, Novo Nordisk) was added and the solution was stirred for 22 hr at the same temperature. 0.54 kg of 40% NaOH solution was added to the reaction solution to neutralize acetic acid and the temperature was raised to 60° C. 40% NaOH (8.64 kg) solution and 30% $H_2O_2$ (5.25 kg) solution were added dropwise for 24 hr to the reaction solution and the same was stirred for 1 hr at the same temperature. The prepared sodium salt of (S)-3,4-dihydroxybutyric acid was identified using NMR analysis.

$^1$H-NMR ($D_2O$, ppm) δ 2.27 (dd, 1H), 2.39 (dd, 1H), 3.41 (dd, 1H), 3.51 (dd, 1H), 3.8–3.9 (m, 1H)

The prepared sodium salt of (S)-3,4-dihydroxybutyric acid was cyclized at 45° C. under reduced pressure in adjusting aqueous sulfuric acid (50%) to pH 1–2 without any separation. The resultant solution extracted with ethyl acetate. The organic layer was neutralized with sodium carbonate. After filtering and concentrating the same, (S)-3-hydroxy-γ-butyrolactone (2.86 kg, 57.2 wt. % of the starch weight used) was obtained.

$^1$H-NMR (CDCl$_3$, ppm) δ 2.28 (dd, 1H), 2.74 (dd, 1H), 4.13 (dd, 1H), 4.32 (dd, 1H), 4.4–4.5 (m, 1H)

EXAMPLE 3
Preparation of (S)-3-hydroxy-γ-butyrolactone

As in the Example 2, however adjusting pH 1~2 of methanesulfonic acid rather than aqueous sulfuric acid (50%) in the cyclization, the same was cyclized at 45° C. under reduced pressure. The resultant solution extracted with ethyl acetate. The organic layer was neutralized with sodium carbonate. After filtrating and concentrating the same, (S)-3-hydroxy-γ-butyrolactone (2.85 kg, 57 wt. % of the starch weight used) was obtained.

$^1$H-NMR (CDCl$_3$, ppm) δ 2.28 (dd, 1H), 2.74 (dd, 1H), 4.13 (dd, 1H), 4.32 (dd, 1H), 4.4–4.5 (m, 1H)

Comparative Example 1
Preparation of (S)-3-hydroxy-γ-butyrolactone from Starch 20 L of water and 5 kg of dried starch were put into a 50 L reactor, and the temperature was raised to 70° C. 40% NaOH (8.64 kg) solution and 30% H$_2$O$_2$ (5.25 kg) solution were added dropwise for 48 hr to the reaction solution and the same was stirred for 1 hr at the same temperature. The same was performed as in Example 2 to obtain (S)-3-hydroxy-γ-butyrolactone (1.1 kg, 22.0 wt. % of starch weight used).

Comparative Example 2
Preparation of (S)-3-hydroxy-γ-butyrolactone from Starch 10 L of 0.5N HCl solution and 5 kg of dried starch were put into a 50 L reactor, and the starch was hydrolyzed for 20 min at 100° C. After cooling the solution to 20° C., the same was neutralized with 100 mL of 40% NaOH solution and the temperature was raised to 70° C. 40% NaOH (8.64 kg) solution and 30% H$_2$O$_2$ (5.25 kg) solution were added dropwise for 48 hr to the reaction solution and the same was stirred for 1 hr at the same temperature. The same was performed as in Example 2 to obtain (S)-3-hydroxy-γ-butyrolactone (1.22 kg, 24.4 wt. % of starch weight used).

Comparative Example 3
Preparation of (S)-3-hydroxy-γ-butyrolactone from Amylose 20 L of water and 5 kg of dried amylose were put into a 50 L reactor, and the temperature was raised to 70° C. 40% NaOH (8.64 kg) solution and 30% H$_2$O$_2$ (5.25 kg) solution were added dropwise for 48 hr to the reaction solution and the same was stirred for 1 hr at the same temperature. The same was performed as in the Example 2 to obtain (S)-3-hydroxy-γ-butyrolactone (1.35 kg, 27.0 wt. % of amylose weight used).

Experimental Example 1
Comparison of (S)-3-hydroxy-γ-butyrolactone Yield Depending on the Source Material For the reaction solutions containing each of the carbohydrates shown in Table 1, oxidation, esterification and cyclization were performed as in the Example 2 to obtain (S)-3-hydroxy-γ-butyrolactone. The yields of (S)-3-hydroxy-γ-butyrolactone are shown in Table 1.

TABLE 1

| Source material (5 kg) | Product (wt. % compared with source material weight) |
|---|---|
| Oligosaccharide of the present invention (Example 2) Polysaccharide | 2.86 kg (57.2 wt. %) |
| Starch | 1.01 kg (22.0 wt. %) |
| Amylose | 1.35 kg (27.0 wt. %) |
| Disaccharide (maltose)[a] | 1.19 kg (23.7 wt. %) |

[a]Examples 1 & 2 of U.S. Pat. Nos. 5,292,939, 5,319,110 & 5,374,773

Table 1 shows that for disaccharide the relative mass conversion yield is low as 23.7 wt. %. On the other hand, if starch is transformed to oligosaccharide with specific enzyme treatment, the relative mass conversion yield is enhanced to 57.2 wt. %, almost two times higher compared with disaccharide. If starch is not treated with enzymes, the relative mass conversion yield is relatively low as 22.0 wt. %.

Experimental Example 2
Optical Purity Analysis of (S)-3-hydroxy-γ-butyrolactone (S)-3-Acetoxy-γ-butyrolactone was synthesized by the following method in order to analyze optical purity of (S)-3-hydroxy-γ-butyrolactone prepared from the present invention and the conventional preparing method.

102 mg (1 mmol) of (S)-3-hydroxy-γ-butyrolactone prepared from each method was dissolved in 3 mL of methylene chloride, and 0.4 mL (5 mmol) of pyridine and 0.47 mL (5 mmol) of acetic anhydride were added to the same. After 3 hr, the reaction was quenched with 1N HCl. (S)-3-Acetoxy-γ-butyrolactone was extracted with the methylene chloride. After work up, the same was purified with silica gel column chromatography. The obtained (S)-3-acetoxy-γ-butyrolactone was dissolved in methylene chloride, and 0.5 μl was taken with syringe for GC analysis. The result is shown in the following Table 2 and FIGS. 1a–c.

TABLE 2

| Source Material | Optical Purity |
|---|---|
| Disaccharide (maltose)[a] | 94% ee |
| Oligosaccharide of the present invention (Example 2) | 99.9% ee |

[a]Examples 1 & 2 of U.S. Pat. Nos. 5,292,939, 5,319,110 & 5,374,773

Figure 1B:
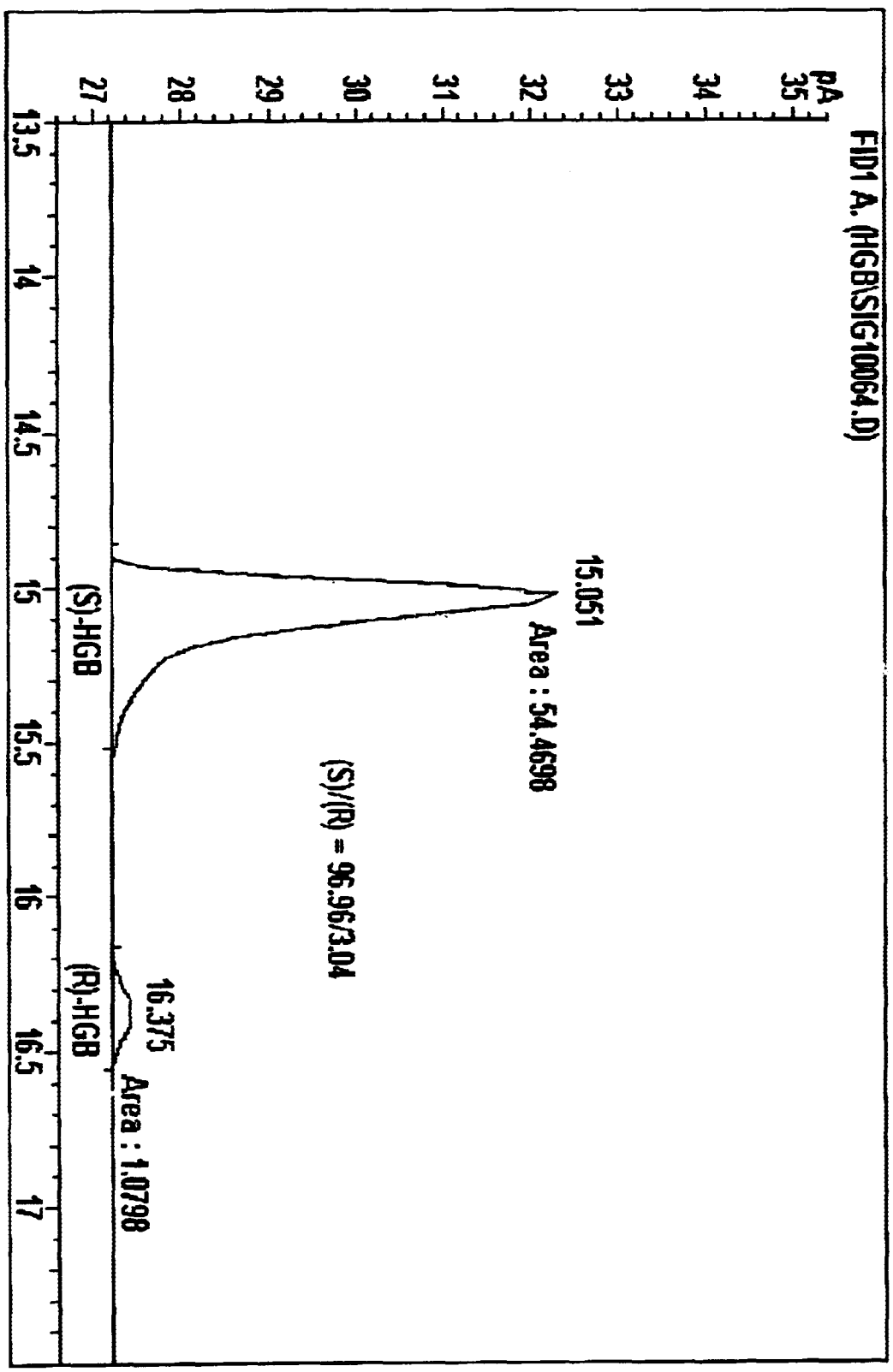
FIG. 1b represents the optical purity analysis results by gas chromatography (GC) of 3-hydroxy-γ-butyrolactone prepared from disaccharide of the conventional method.
Figure 1C:
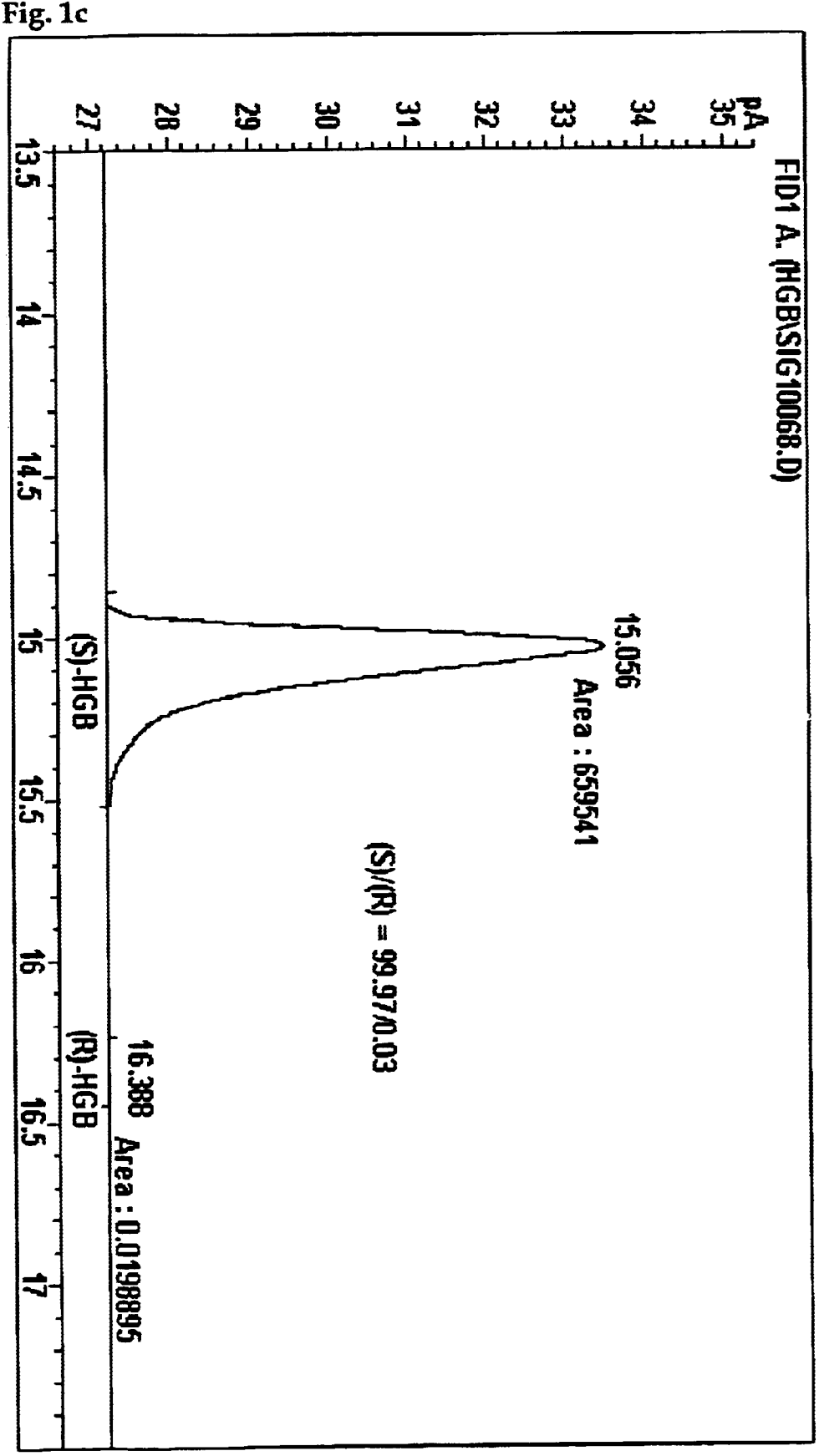
FIG. 1c represents the optical purity analysis results by gas chromatography (GC) of 3-hydroxy-γ-butyrolactone prepared from oligosaccharide of the present invention.

To improve the medicinal efficiency and minimize the side effect, more than 99.5%ee of high optical purity is required for chiral compounds. Table 2 and FIGS. 1a–c show that the optical purity of (S)-3-hydroxy-γ-butyrolactone prepared from the present invention is very high as 99.9% ee. So, the same is very useful for the intermediates of other chiral compounds. The results are illustrated in FIGS. 1a, 1b and 1c, respectively.

The preparing method of the present invention gives optically pure (S)-3-hydroxy-γ-butyrolactone, which is very useful for industrial uses because the by-product formation is minimized and the purification process is very simple. It comprises alkaline oxidation of α-(1,4) linked oligosaccharide from the enzymatic reaction of starch in a specific condition followed by cyclizing to afford the target product. The present invention has overcome the disadvantage of using expensive metal catalyst for selective asymmetric reduction, and enables easy preparation from inexpensive natural product having optically pure chiral center, thereby the industrial utility as chiral intermediates of various medicine can be maximized. Furthermore, the relative mass conversion yield is almost double compared with disaccharides.

What is claimed is:

1. A process for producing optically pure (S)-3-hydroxy-γ-butyrolactone expressed by Formula 1 from polysaccharide source, comprising:
   (a) enzymatic reaction of starch to α-(1,4) linked oligosaccharide expressed by Formula 2;
   (b) oxidation of the oligosaccharide with an oxidant in a base to prepare a metal salt of (S)-3,4-dihydroxybutyric acid expressed by Formula 3, wherein said oxidation comprises adding the oxidant and the base continuously over the course of the reaction; and
   (c) cyclization of the prepared salt of (S)-3,4-dihydroxybutyric acid in the presence of an acid catalyst without additional separation and purification process to form (S)-3-hydroxy-γ-butyrolactone expressed by the Formula 1,

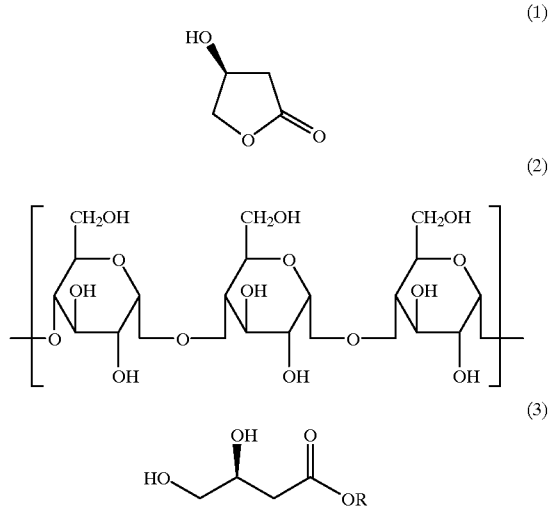

wherein R represents an alkali metal atom or an alkaline earth metal atom.

2. The process according to claim 1, wherein said enzymatic reaction is performed in water or in pH 4–8 buffer solution.

3. The process according to claim 1, wherein said enzymatic reaction is comprises an α-amylase enzymatic reaction followed by an pullulanase enzymatic reaction.

4. The process according to claim 3, wherein said α-amylase enzymatic reaction is performed under conditions of a pH ranging from 4.0–8.0 and a temperature ranging from 40–120° C.

5. The process according to claim 3, wherein said α-amylase is used in an amount ranging from 0.001–10 wt. % of said starch.

6. The process according to claim 3, wherein said pullulanase enzymatic reaction is performed under conditions of a pH ranging from 4.0–8.0 and a temperature ranging from 40–120° C.

7. The process according to claim 3, wherein said pullulanase is used in an amount ranging from 0.001–10 wt. % of said starch.

8. The process according to claim 3, wherein α-amylase remaining after the α-amylase enzymatic reaction is inactivated under conditions of a pH ranging from 2.0–4.5 and a temperature ranging from 60–150° C., before the pullulanase enzymatic reaction is performed.

9. The process according to claim 1, wherein said oxidation is performed at a temperature ranging from 30–65° C.

10. The process according to claim 1, wherein the base used in said oxidation is selected from alkali metal hydroxides and alkaline earth metal hydroxides.

11. The process according to claim 10, wherein said base is sodium hydroxide.

12. The process according to claim 1, wherein said base is used in an amount ranging from 1–3 equivalents per molar glucose unit of starch.

13. The process according to claim 10, wherein said base is used in an amount ranging from 1–3 equivalents per molar glucose unit of starch.

14. The process according to claim 1, wherein the oxidant used in said oxidation is selected from hydrogen peroxide, alkali metal peroxides, alkaline earth metal peroxides and alkyl hydroperoxides.

15. The process according to claim 14, wherein said oxidant is hydrogen peroxide.

16. The process according to claim 14, wherein said oxidant is t-butylhydroperoxide.

17. The process according to claim 1, wherein said oxidant is used in an amount ranging from 1–3 equivalents per molar glucose unit of starch.

18. The process according to claim 14, wherein said oxidant is used in an amount ranging from 1–3 equivalents per molar glucose unit of starch.

19. The process according to claim 1, wherein said oligosaccharide has from 3–50 glucose units.

20. The process according to claim 1, wherein the acid catalyst used in said cyclization is an inorganic acid selected from hydrochloric acid, sulfuric acid, phosphoric acid and nitric acid.

21. The process according to claim 1, wherein acid catalyst used in the said cyclization is an organic acid selected from fluoroalkylsulfonic acid, aralkylsulfonic acid, hydrate of aralkylsulfonic acid and trifluoroacetic acid.

22. The process according to claim 1, wherein the said cyclization is performed at a temperature ranging from 30 to 80° C.

23. A process according to claim 1, wherein the continuous addition of the oxidant and the base comprises drop wise additions.

24. A process according to claim 1, wherein the oxidant and the base are added over a period of from 6 to 36 hours.

* * * * *

UNITED STATES PATENT AND TRADEMARK OFFICE
CERTIFICATE OF CORRECTION

PATENT NO. : 6,713,290 B2 Page 1 of 1
APPLICATION NO. : 09/946449
DATED : March 30, 2004
INVENTOR(S) : Young Mi Park et al.

It is certified that error appears in the above-identified patent and that said Letters Patent is hereby corrected as shown below:

On the title page, item (75), in the Inventors, lines 5-6, "Dae Hwang, Il," should read --Dae Il Hwang,--.

On the title page, item (63), in the Related U.S. Application Data, "Continuation" should read --Continuation-in-Part--.

On the title page, item (30), in the Foreign Application Priority Data, "Jul. 24, 2001" should read --Jul. 24, 1998--.

In claim 3, column 11, line 46, "reaction is comprises" should read --reaction comprises--.

Signed and Sealed this

Fifth Day of February, 2008

JON W. DUDAS
*Director of the United States Patent and Trademark Office*